United States Patent
Vandroux et al.

(10) Patent No.: US 10,831,287 B2
(45) Date of Patent: Nov. 10, 2020

(54) SYSTEM AND METHOD FOR RECEIVING USER INPUT

(71) Applicant: GE PRECISION HEALTHCARE LLC, Wauwatosa, WI (US)

(72) Inventors: Stéphane Vandroux, Paris (FR); Gauthier Libaux, Versailles (FR)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 16/298,246

(22) Filed: Mar. 11, 2019

(65) Prior Publication Data

US 2020/0293122 A1    Sep. 17, 2020

(51) Int. Cl.
*G06F 3/0338*    (2013.01)
*G06F 3/038*    (2013.01)
*A61B 6/00*    (2006.01)

(52) U.S. Cl.
CPC ............ *G06F 3/0338* (2013.01); *A61B 6/467* (2013.01); *G06F 3/0383* (2013.01)

(58) Field of Classification Search
CPC ...... G06F 3/0338; G06F 3/0383; A61B 6/467
See application file for complete search history.

(56) References Cited

U.S. PATENT DOCUMENTS

| | | | |
|---|---|---|---|
| 6,840,113 B2 | 1/2005 | Fukumura et al. | |
| 7,495,405 B2 | 2/2009 | Sugiura | |
| 8,731,218 B2 * | 5/2014 | Yeates | H01H 9/0228 381/105 |
| 9,293,063 B2 | 3/2016 | Qin et al. | |
| 9,823,781 B2 | 11/2017 | Ludwig et al. | |
| 10,042,479 B2 | 8/2018 | Ludwig et al. | |
| 10,065,111 B1 | 9/2018 | Patel et al. | |
| 10,248,228 B2 * | 4/2019 | Minyu | G06F 3/0487 |
| 2009/0009491 A1 * | 1/2009 | Grivna | G06F 3/033 345/184 |
| 2012/0154313 A1 * | 6/2012 | Au | G06F 3/04883 345/173 |
| 2014/0165770 A1 * | 6/2014 | Abri | A61B 34/30 74/490.01 |

FOREIGN PATENT DOCUMENTS

WO    WO-2019099504 A1 *    5/2019    ............ A61B 34/37
WO    WO-2019217882 A1 *    11/2019    ............ A61B 17/00

* cited by examiner

*Primary Examiner* — Bryan Earles
(74) *Attorney, Agent, or Firm* — Grogan, Tuccillo & Vanderleeden, LLP

(57) ABSTRACT

A user input device is provided. The user input device includes: a body; one or more sensors operative to detect a contact pressure arrangement applied to the body; and a controller in electronic communication with the one or more sensors. The controller is operative to: determine that the contact pressure arrangement corresponds to a pinching action; and manipulate a control signal based at least in part on the contact pressure arrangement.

20 Claims, 6 Drawing Sheets

SYSTEM AND METHOD FOR RECEIVING USER INPUT

BACKGROUND

Technical Field

Embodiments of the present invention relate generally to human machine interfaces ("HMI"), and more specifically, to a system and method for receiving user input.

Discussion of Art

HMIs are systems which facilitate interaction between humans and machines. Many modern HMIs have joysticks and/or other types of movable devices, e.g., dials, that allow a human operator to provide input to a machine. Such devices often convert physical pressure, e.g., movement of a joystick, into electrical signals that cause the machine to take an action. For example, movement of a joystick may cause corresponding movement of a cursor on a graphical user interface ("GUI") or movement of a mechanical arm.

Many HMIs, however, are unable to distinguish between desired user input, e.g., intentional manipulation of a joystick by an operator, from undesired user input, e.g., accidental contact between the operator and the joystick such as an arm brushing against the joystick. As will be understood, undesired user input can be problematic, especially with respect to medical machines. For example, the x-ray emitters of many x-ray imaging systems are often controlled by a joystick, wherein accidental contact between the joystick and an operator may result in unintended movement of the x-ray emitter, which in turn, could result in unsatisfactory images.

What is needed, therefore, is an improved system and method for receiving user input.

BRIEF DESCRIPTION

In an embodiment, a user input device is provided. The user input device includes: a body; one or more sensors operative to detect a contact pressure arrangement applied to the body; and a controller in electronic communication with the one or more sensors. The controller is operative to: determine that the contact pressure arrangement corresponds to a pinching action; and manipulate a control signal based at least in part on the contact pressure arrangement.

In another embodiment, a method of controlling a device is provided. The method includes: detecting, via one or more sensors, a contact pressure arrangement applied to a body of a user input device; determining via a controller in electronic communication with the one or more sensors that the contact pressure arrangement corresponds to a pinching action; and manipulating a control signal via the controller based at least in part on the contact pressure arrangement.

In still yet another embodiment, a non-transitory computer readable medium storing instructions is provided. The stored instructions adapt a controller to: detect, via one or more sensors, a contact pressure arrangement applied to a body of a user input device; determine that the contact pressure arrangement corresponds to a pinching action; and manipulate a control signal based at least in part on the contact pressure arrangement.

DRAWINGS

The present invention will be better understood from reading the following description of non-limiting embodiments, with reference to the attached drawings, wherein below:

DETAILED DESCRIPTION

Figure 1:
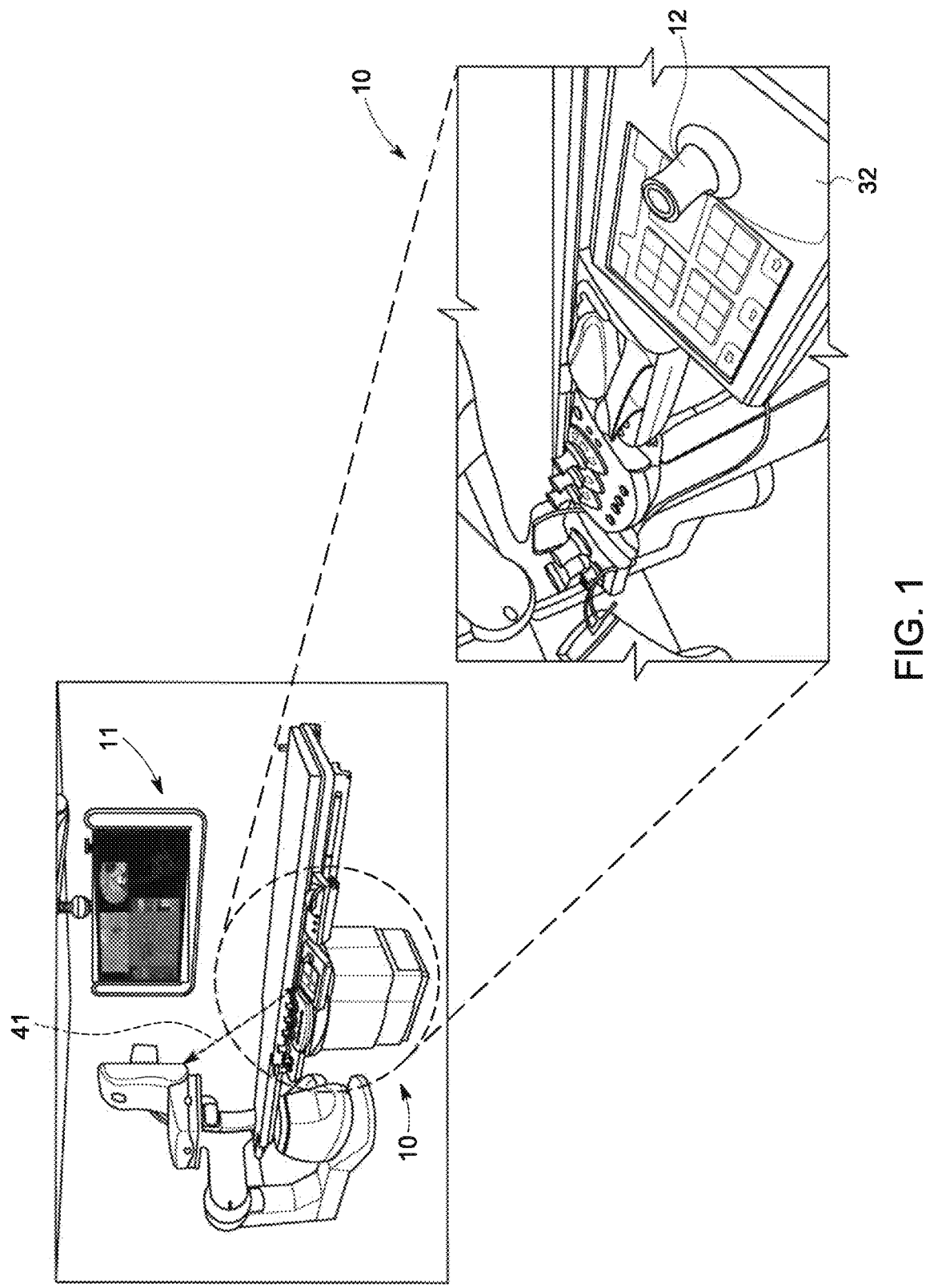
FIG. 1 is a diagram of a system for receiving user input, wherein the system is disposed in an x-ray imaging machine, in accordance with an embodiment of the present invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," "approximately" and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Further, while the embodiments disclosed herein are described with respect to an interventional x-ray imaging system, it is to be understood that embodiments of the present invention may be applicable to other types of imaging systems, and/or any device/system that includes a physical user input device/control which is typically pinched by an operator during use. Further still, as will be appreciated, embodiments of the present invention related imaging systems may be used to analyze tissue generally and are not limited to human tissue. Yet further still, while the embodiments herein are disclosed as being directed towards x-ray imaging, it will be understood that embodiments of the present invention may utilize other types of electromagnetic radiation.

Figure 2:
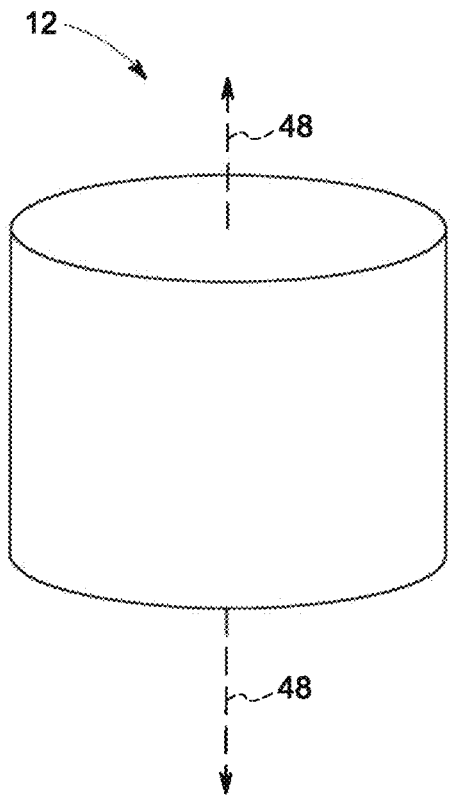
FIG. 2 is perspective view of a body of the system of FIG. 1, in accordance with an embodiment of the present invention.

Referring now to FIG. 1, a user input device/system 10 in accordance with an embodiment of the present invention is shown, wherein the input device 10 is incorporated into an interventional x-ray system 11. As shown in FIG. 1, the user input device 10 includes a body 12, e.g., a joystick, rocker, or other type of object having a control surface, which is depicted in perspective views in FIGS. 2 and 4 and in top-down views in FIGS. 3, 5 and 7-9. The user input device 10 further includes one or more sensors 14, 16, 18, 20, 22, 24, 26, 28 and 30 (FIGS. 4 and 5), and a controller/processor 32. The sensors 14, 16, 18, 20, 22, 24, 26, 28 and 30 electronically communicate with the controller 32 and are operative to detect a contact pressure arrangement 34, 36 and 38 (FIG. 3) applied to the body 12. As used herein, the term "contact pressure" refers to any type of pressure and/or contact imparted on the body 12 of the input device 10 via contact with another object. Accordingly, the term "contact pressure arrangement", as used herein, refers to a collection of points 34, 36 and 38 of contact pressure along the body 12 of the user input device 10, e.g., the points of contact between the hand 40 of an operator and the body 12 as shown in FIG. 6. In embodiments, the sensors 14, 16, 18, 20, 22, 24, 26, 28 and 30 may be electrical conduction-based, e.g., capacitors, mechanical-based, e.g., springs, and/or any other type of sensors capable of detecting contact between the hand 40 of an operator and the body 12 of the user input device 10.

The controller 32 is operative to: determine that the contact pressure arrangement 34, 36 and 38 corresponds to a pinching action (best seen in FIG. 6); and to manipulate a control signal 41 (FIG. 1) based at least in part on the contact pressure arrangement 34, 36 and 38. The term "control signal", as used herein, refers to an electrical, optical, and/or mechanical (to include hydraulic and/or pneumatic) mechanism that achieves a desired effect, e.g., moving a cursor on a GUI or a mechanical arm. The term "pinching action", as used herein, refers to the act/motion of griping the body 12 via an operator's digits, e.g., between the thumb 42 and one or more fingers 44 and 46 as shown in FIG. 6. While FIG. 6 depicts a three digit pinching action of the body 12, it is to be understood that the pinching action may be between the thumb 42 and a single finger 44, or between the thumb 42 and three or more fingers. It will be yet further understood that, in embodiments, the digits may be artificial, e.g., robotic fingers and/or other objects capable of pinching the body 12.

In embodiments, the controller 32 determines that the contact pressure arrangement 34, 36 and 38 corresponds to the pinching action independently of the orientation of the contact pressure arrangement 34, 36 and 38 being aligned with pre-determined fixed positions with respect to the body 12. In other words, the controller 32 is able to determine that the operator is pinching the body 12 regardless of the orientation of the digits 42, 44 and 46 around the body 12. The controller 32 may also manipulate the control signal only while the contact pressure arrangement 34, 36 and 38 corresponds to the pinching action. As it is highly unlikely for an operator to inadvertently apply a contact pressure arrangement to the body 12 corresponding to a pinching action, some embodiments of the present invention provide for a user input device that reduces the likelihood of undesired user inputs into a system/machine due to inadvertent/accidental/unintended contact between the operator and the user input device 10.

Figure 3:
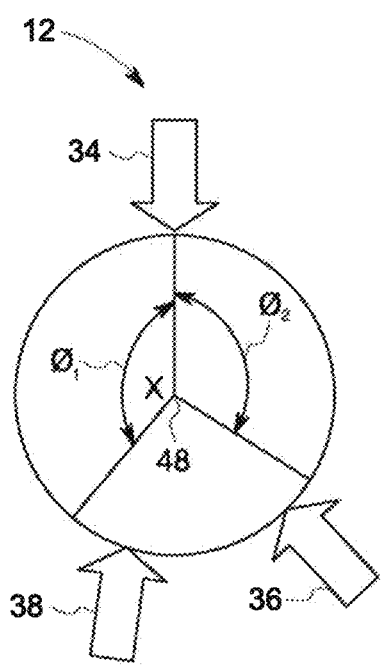
FIG. 3 is a top-down view of the body of FIG. 2, in accordance with an embodiment of the present invention.

As illustrated in FIG. 3, in embodiments, the controller 32 (FIG. 1) may determine that the contact pressure arrangement 34, 36, 38 corresponds to a pinching action based on pre-determined angular ranges/limits of the points within the contact pressure arrangement with respect to each other and/or to a central axis 48 of the body 12, e.g., within one or more limits/ranges defined by one or more angular distances $\varnothing_1$ and/or $\varnothing_2$ between one or more of the points 34, 36 and 38 within the contact pressure arrangement about the central axis 48. In embodiments, $\varnothing_1$ and/or $\varnothing_2$ may range from about 0° to about 180°. In certain aspects of the present invention, $\varnothing_1$ and/or $\varnothing_2$ may be about 135°. In some embodiments, $\varnothing_1$ and $\varnothing_2$ may be different from each other, e.g., $\varnothing_1$ may be about 45° and $\varnothing_2$ may be about 10°.

As such, in embodiments, the controller 32 determines that the contact pressure arrangement corresponds to a pinching action when at least one point 36 and/or 38 corresponding to a finger 44 and/or 46 (FIG. 6) is at least approximately $\varnothing_1$ and/or $\varnothing_2$, respectively, from a point 34 corresponding to the thumb 42 (FIG. 6). Thus, in embodiments, at least two points, e.g., the thumb and one finger, within the contact pressure arrangement are at least approximately $\varnothing_1$ and/or $\varnothing_2$ of each other.

In other aspects of the present invention, the controller 32 determines that the contact pressure arrangement corresponds to a pinching action when all points 36 and/or 38, within the contact pressure arrangement corresponding to fingers, e.g., 44 and 46, are at least approximately $\varnothing_1$ and/or $\varnothing_2$, respectively, from the point 34 corresponding to the thumb 42. Thus, in embodiments where $\varnothing_1$ and/or $\varnothing_2$=135°, at least two points are disposed at least within 135° of each other and no more than approximately 225° of each other with respect to the central axis 48.

Figure 4:
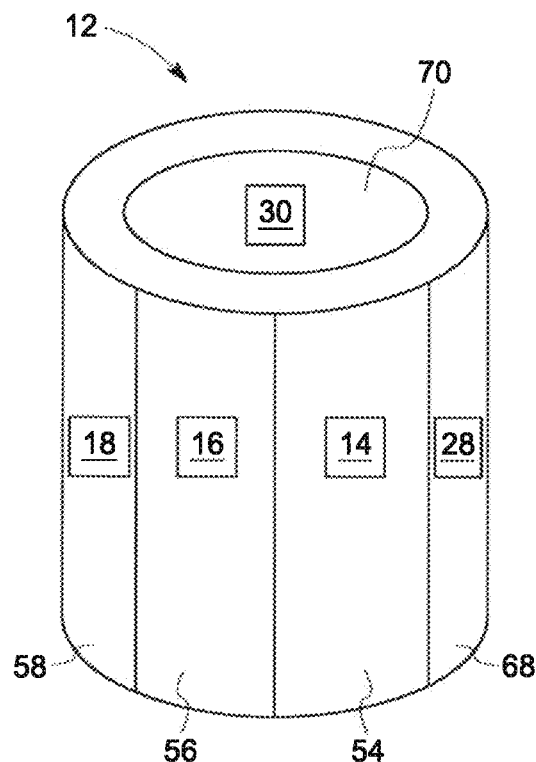
FIG. 4 is another perspective view of the body of FIG. 2, in accordance with an embodiment of the present invention.
Figure 5:
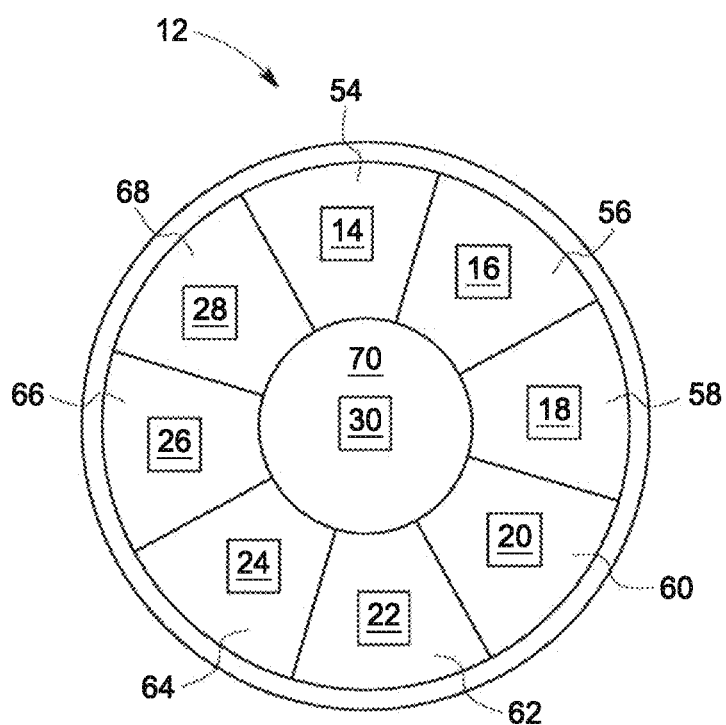
FIG. 5 is another top-down view of the body of FIG. 2, in accordance with an embodiment of the present invention.
Figure 6:
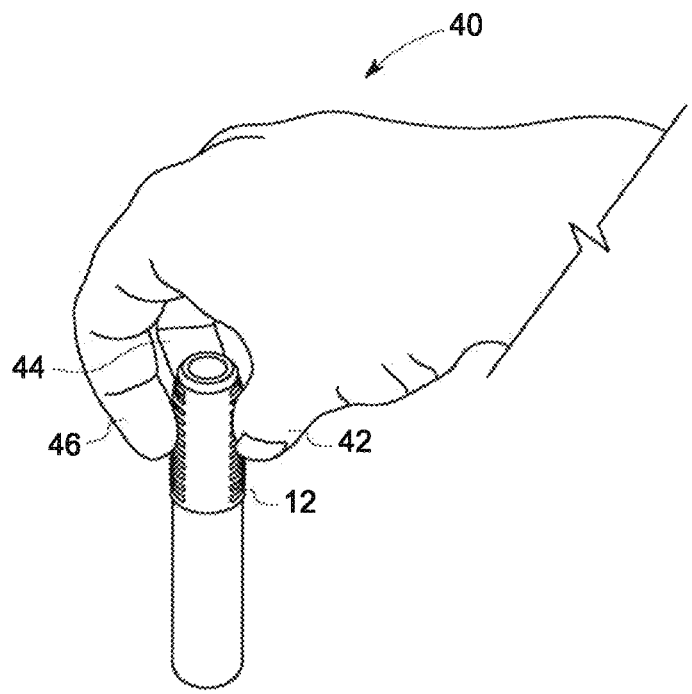
FIG. 6 is a diagram of an operator pinching the body of FIG. 2, in accordance with an embodiment of the present invention.

Moving to FIGS. 4 and 5, in embodiments, the one or more sensors 14, 16, 18, 20, 22, 24, 26, 28 and 30 may define one or more trigger zones 54, 56, 58, 60, 62, 64, 66, 68 and 70 that correspond to different possible points of contact pressure of a possible contact pressure arrangement. While FIG. 5 depicts a one-to-one relationship between the sensors 14, 16, 18, 20, 22, 24, 26, 28 and 30 and the trigger zones 54, 56, 58, 60, 62, 64, 66, 68 and 70, it is to be understood that each trigger zone may be defined by two or more sensors and/or each sensor may define two or more trigger zones.

Figure 7:
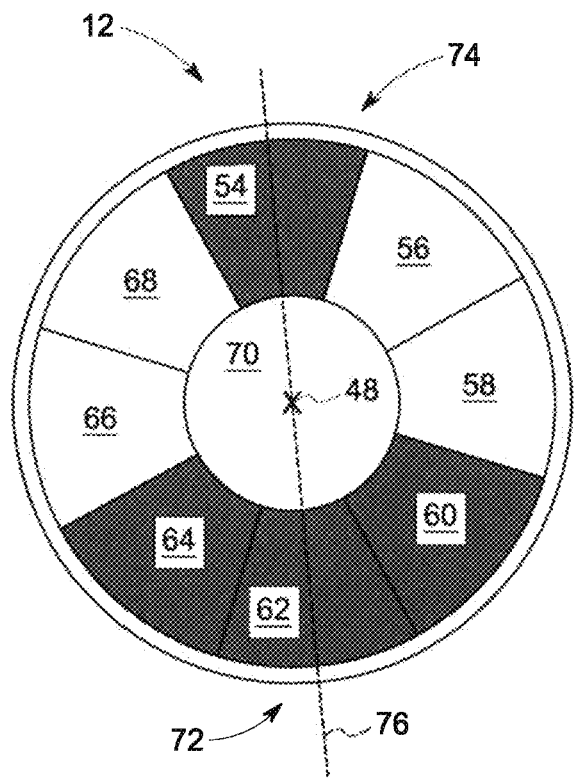
FIG. 7 is another top-down view of the body of FIG. 2, in accordance with an embodiment of the present invention.

Accordingly, turning to FIG. 7, in embodiments, the controller 32 (FIG. 1) may determine that a detected contact pressure arrangement corresponds to a pinching action by detecting a first grouping 72 of one or more activated trigger zones 60, 62 and 64, and detecting a second grouping 74 of one or more activated trigger zones, 54, centered opposite the first grouping 72 about the central axis 48. As used herein with respect to a "trigger zone", the terms "activated" and "inactivated" respectively mean that at least one sensor defining the trigger zone is detecting or failing to detect contact pressure between the body 12 of the user input device 10 and another object, e.g., the hand 40 of an operator. For example, as shown in FIG. 7, the first 72 and second 74 groupings are centered opposite each other, i.e., the center trigger zone of the first grouping 72, e.g., zone 62, is disposed exactly, or approximately, across from the center trigger zone of the second grouping 74, e.g., zone 54, along a line 76 that passes through the center of both groupings 72 and 74, zones 62 and 54 and the central axis 48. As used herein, the term "center zone" refers to the trigger zone of a grouping that is at, or substantially close to, the center of the grouping about the central axis 48.

Figure 8:
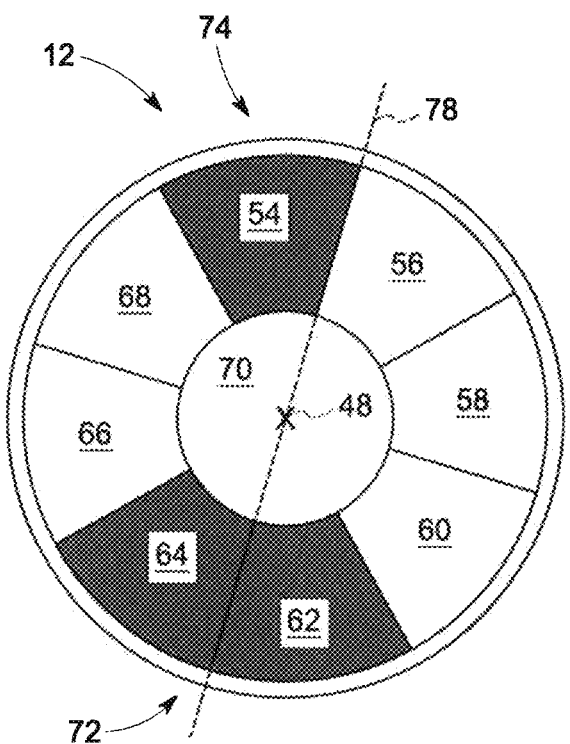
FIG. 8 is another top-down view of the body of FIG. 2, in accordance with an embodiment of the present invention.

While the foregoing example shows the center zones, e.g., 62 and 54, of each grouping 72 and 74 being exactly centered across from each other, in embodiments, the center zones of the groupings 72 and 74 may be slightly offset, e.g., as shown in FIG. 8 where a grouping, e.g., 72, has an even number of contiguous zones such that the grouping has no zone exactly in the center of the grouping. In such embodiments, the center zone of the grouping may be either of the zones closest to the actual center of the grouping, e.g., zones 64 or 62 for grouping 72 or zones 54 or 56 in grouping 74.

In embodiments, the controller 32 may select one or more trigger zones that define the second grouping 74 based on the activated trigger zones detected in the first grouping 72, where the controller 32 determines that the body 12 is being pinched when the trigger zones selected as defining the second grouping 74 are detected as being activated, i.e., touched. In other words, the controller 32 may determine which trigger zones are eligible to be in the second grouping 74 based on the number and locations of activated trigger zones the controller 32 detects in the first grouping 72. In such embodiments, the center zone of the second grouping 74, e.g., zone 54, may be defined/selected by the controller 32 as the zone closest to a line 78 extending through the actual center of the first grouping 72 and the central axis 48. While FIG. 8 shows zone 54 as being selected as the center zone of the second grouping 74, as well as the only zone within the grouping 74, it will be understood that, in embodiments, zone 56 could have been selected instead or in addition to zone 54.

Figure 9:
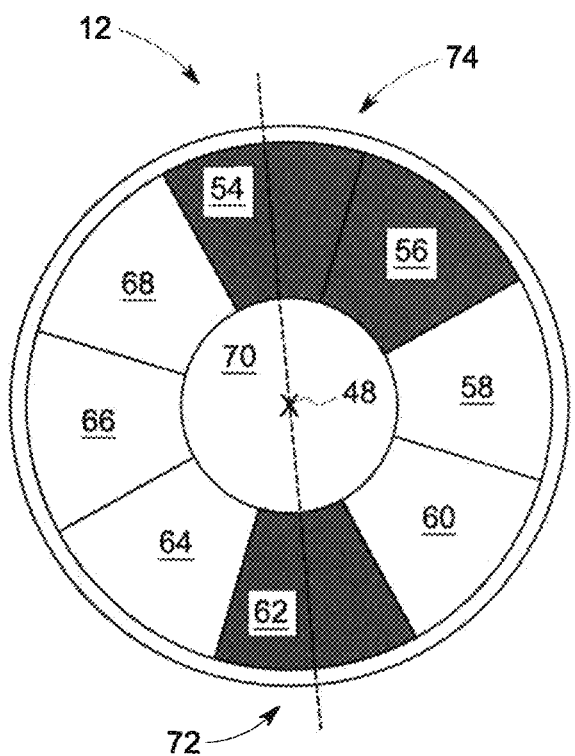
FIG. 9 is another top-down view of the body of FIG. 2, in accordance with an embodiment of the present invention.

Referring now to FIGS. 8 and 9, in embodiments, the controller 32 (FIG. 1) determines that the contact pressure arrangement corresponds to a pinching action when either of the following cases is true: Case 1) the first grouping 72 includes only a single activated trigger zone 62 and the second grouping 74 includes two or more activated trigger zones 54 and 56, as shown in FIG. 9; or Case 2) the first grouping 72 includes two or more activated trigger zones 62 and 64 and the second grouping 74 includes only a single activated trigger zone 54, as shown in FIG. 8. In such embodiments, the first grouping 72 may be the grouping detected first in time, i.e., before the second grouping 74, wherein, as will be appreciated, Case 1 (FIG. 9) corresponds to a scenario where the thumb 42 (FIG. 6) of an operator contacts the body 12 before the fingers 44 and 46 (FIG. 6), and Case 2 (FIG. 8) corresponds to a scenario where the fingers 44 and 46 of an operator contact the body 12 before the thumb 42. In embodiments, the grouping, e.g., 72 or 74, having two or more points must be arranged such that all points within the grouping are contiguous.

Figure 10:
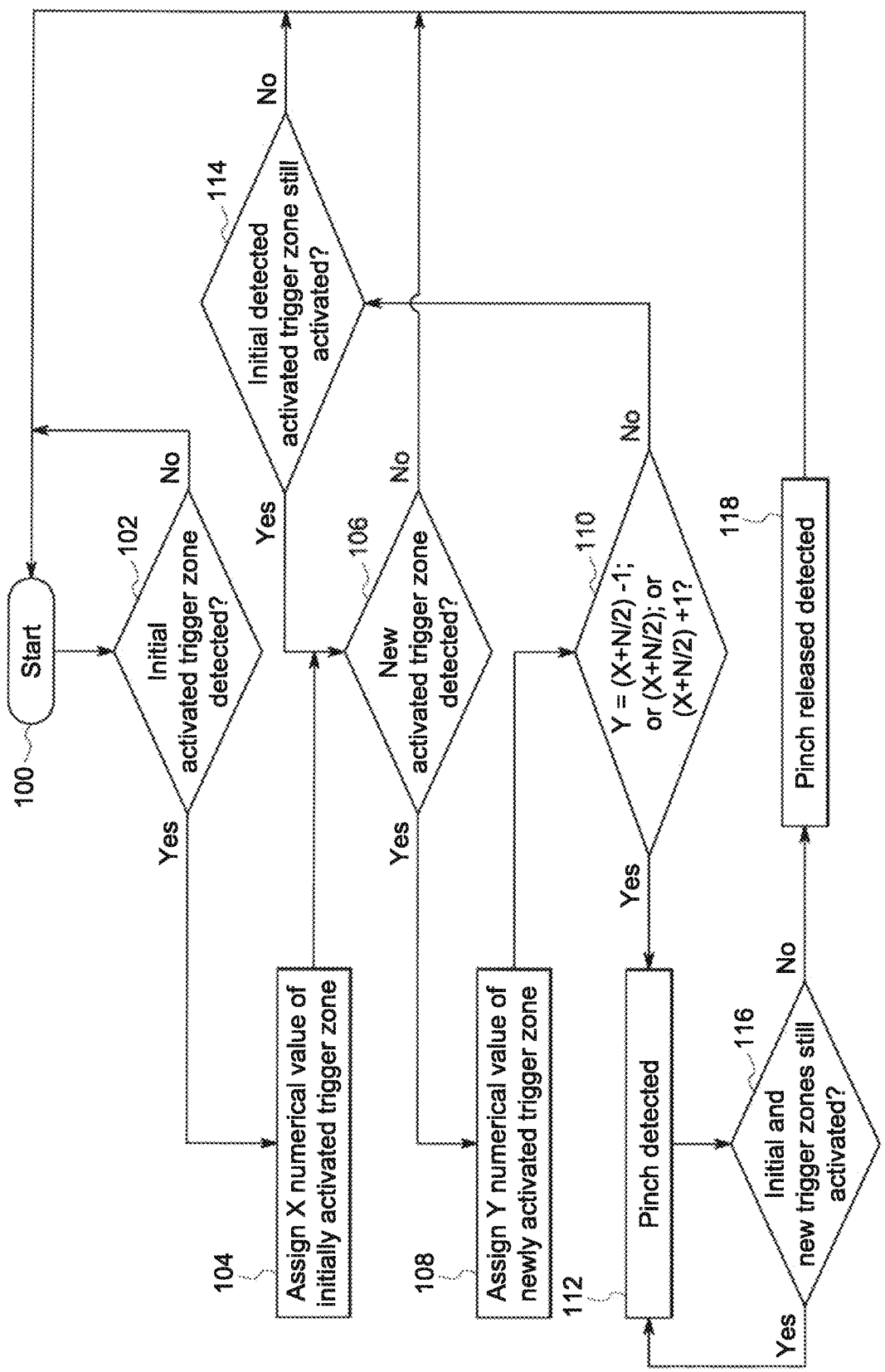
FIG. 10 is a flow chart depicting a method of receiving user input utilizing the system of FIG. 1, in accordance with an embodiment of the present invention.

Turning to FIG. 10, in embodiments, the controller 32 (FIG. 1) may detect a pinching action as follows. The controller 32 initially waits 100 until an initial trigger zone 54, 56, 58, 60, 62, 64, 66, 68 and/or 70 (FIGS. 5 and 7-9) is detected 102 as being activated. The controller 32 then assigns 104 a variable X the numeric value of the initially detected activated trigger zone and then tests 106 to see if another/subsequent activated trigger zone has been newly detected.

Referring briefly to FIG. 9, as will be understood, the numeric value of a trigger zone is the number representing the sequential order of the trigger zone with respect to other trigger zones on the body 12 in either a clockwise or counter-clockwise direction about the central axis 48 from an arbitrarily selected starting point. For example, if zone 54 is selected as the starting point, the zones would have the following numeric values in the clockwise direction about axis 48: zone 54=one (1); zone 56=two (2); zone 58=three (3); zone 60=four (4); zone 62=five (5); zone 64=six (6); zone 66=seven (7); zone 68=eight (8), and, optionally, zone 70=nine (9) as it represents the top of the body 12. While the accompanying figures depict the user input device 10 as having nine (9) trigger zones 54, 56, 58, 60, 62, 64, 66, 68 and 70, it will be understood that, in embodiments, the number of zones may be two (2) or greater.

Returning back to FIG. 10, upon detecting 106 a newly activated trigger zone, the controller 32 assigns 108 the variable Y the numerical value of the newly activated trigger zone and then tests 110 to see if Y satisfies any the following three conditions: (X+N/2)−1; (X+N/2); or (X+N/2)+1, wherein N is the total number of trigger zones on the body 12. Satisfaction of any of these three conditions may be interpreted 112 by the controller 32 as an indication that the body 12 is being pinched. If, however, Y fails to satisfy any of the three foregoing conditions, the controller 32 checks 114 to see if the initially activated trigger zone is still activated which, if true, causes the controller 32 to wait for the next newly activated trigger zone, and if false, causes the controller 32 to again test 102 for an initially activated trigger zone. If a pinch is detected 112, then the controller 32 allows for modulation of the control signal 41 (FIG. 1) while both the initial and subsequent activated trigger zones, i.e., the trigger zones corresponding to X and Y, remain activated as shown by the loop between 112 and 116. If the controller 32 detects that either of the trigger zones corresponding to X and Y are inactive, the controller 32 then detects 118 that the pinch has been released and no longer allows for modulation of the control signal 41.

Finally, it is also to be understood that the device/system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the device/system may include at least one processor and system memory/data storage structures, which may include random access memory (RAM) and read-only memory (ROM). The at least one processor of the device/system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the device/system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random-access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment of the present invention, a user input device is provided. The user input device includes: a body; one or more sensors operative to detect a contact pressure arrangement applied to the body; and a controller in electronic communication with the one or more sensors. The controller is operative to: determine that the contact pressure arrangement corresponds to a pinching action; and manipulate a control signal based at least in part on the contact pressure arrangement. In certain embodiments, the controller determines that the contact pressure arrangement corresponds to the pinching action independently of the orientation of the contact pressure arrangement being aligned with pre-determined fixed positions with respect to the body. In certain embodiments, the controller determines that the contact pressure arrangement corresponds to the pinching action when the contact pressure arrangement includes two points of contact pressure that are disposed at least approximately 135° of each other with respect to a central axis of the body. In certain embodiments, the two points of contact pressure are disposed no more than approximately 225° of each other with respect to the central axis. In certain embodiments, the one or more sensors each define a distinct trigger zone corresponding to a different possible point of contact pressure of the contact pressure arrangement. In certain embodiments, the controller determines that the contact pressure arrangement corresponds to the pinching action by: detecting a first grouping of one or more activated trigger zones; and detecting a second grouping of or more activated trigger zones centered opposite the first grouping about the body. In certain embodiments, the controller determines that the contact pressure arrangement corresponds to the pinching action when: the first grouping includes only a single activated trigger zone and the second grouping includes two or more activated trigger zones; or the first grouping includes two or more activated trigger zones and the second grouping includes only a single activated trigger zone. In certain embodiments, the body is configured to be integrated into a medical imaging device. In certain embodiments, the controller is further operative to manipulate the control signal only while the contact pressure arrangement corresponds to the pinching action.

Other embodiments provide for a method of controlling a device. The method includes: detecting, via one or more sensors, a contact pressure arrangement applied to a body of a user input device; determining via a controller in electronic communication with the one or more sensors that the contact pressure arrangement corresponds to a pinching action; and manipulating a control signal via the controller based at least in part on the contact pressure arrangement. In certain embodiments, determining via a controller in electronic communication with the one or more sensors that the contact pressure arrangement corresponds to a pinching action is independent of the orientation of the contact pressure arrangement being aligned with pre-determined fixed positions with respect to the body. In certain embodiments, determining via a controller in electronic communication with the one or more sensors that the contact pressure arrangement corresponds to a pinching action includes detecting via the controller that two points of contact pressure of the contact pressure arrangement are disposed at least approximately 135° of each other with respect to a central axis of the body. In certain embodiments, determining via a controller in electronic communication with the one or more sensors that the contact pressure arrangement corresponds to a pinching action further includes detecting via the controller that the two points of contact pressure are disposed no more than approximately 225° of each other with respect to a central axis of the body. In certain embodiments, the one or more sensors each define a distinct trigger zone corresponding to a different possible point of contact pressure of the contact pressure arrangement, and determining via a controller in electronic communication with the one or more sensors that the contact pressure arrangement corresponds to a pinching action further includes: detecting via the controller a first grouping of one or more activated trigger zones; and detecting via the controller a second grouping of one or more activated trigger zones centered opposite the first grouping about the body. In certain embodiments, the controller determines that the contact pressure arrangement corresponds to the pinching action when: the first grouping includes only a single activated trigger zone and the second grouping includes two or more activated trigger zones; or the first grouping includes two or more activated trigger zones and the second grouping includes only a single activated trigger zone. In certain embodiments, the controller manipulates the control signal only while the contact pressure arrangement corresponds to the pinching action.

Yet still other embodiments provide for a non-transitory computer readable medium storing instructions. The stored instructions adapt a controller to: detect, via one or more sensors, a contact pressure arrangement applied to a body of a user input device; determine that the contact pressure arrangement corresponds to a pinching action; and manipulate a control signal based at least in part on the contact pressure arrangement. In certain embodiments, the instructions further adapt the controller to determine that the contact pressure arrangement corresponds to the pinching action independently of the orientation of the contact pressure arrangement being aligned with pre-determined fixed positions with respect to the body. In certain embodiments, the instructions further adapt the controller to determine that the contact pressure arrangement corresponds to a pinching action by: detecting that two points of contact pressure of the contact pressure arrangement are disposed at least approximately 135° of each other with respect to a central axis of the body. In certain embodiments, the instructions further adapt the controller to manipulate the control signal only while the contact pressure arrangement corresponds to the pinching action.

Accordingly, as will be appreciated, by providing for a device and method of determining when a user input device is being pinched based at least in part on a detected contact pressure arrangement, some embodiments of the present invention reduce and/or eliminate the risk of unintended inputs to a user input device. In other words, some embodiments of the present invention reduce the likelihood that inadvertent contact between an object, e.g., the arm of an operator, will be received/interpreted as intended user input, which in turn, provides for safer and more efficient user input control devices.

Further, by basing, at least in part, the determination of whether a detected contact pressure arrangement corresponds to a pinching action on the angular distance(s) between contact pressure points within the arrangement, as opposed to predetermined fixed positions, some embodiments of the present invention provide for a user input device that detects pinching actions regardless of the rotational orientation of the digits, i.e., thumb and finger(s), of the operator with respect to the rotational orientation of the control device. Thus, some embodiments of the present invention provide for a more flexible and accurate user input device.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A user input device comprising:
    a body with at least first and second surfaces;
    one or more sensors on at least one surface operative to detect a contact pressure arrangement applied to the body; and
    a controller in electronic communication with the one or more sensors and operative to:
        determine that the contact pressure arrangement of three or more sensors corresponds to a pinching action; and
        upon recognition of said pinching action, enabling a control signal.

2. The user input device of claim 1, wherein the controller determines that the contact pressure arrangement corresponds to the pinching action independently of the orientation of the contact pressure arrangement being aligned with pre-determined fixed positions with respect to the body.

3. The user input device of claim 1, wherein the controller determines that the contact pressure arrangement corresponds to the pinching action when the contact pressure arrangement includes two points of contact pressure that are disposed at least approximately 135° of each other with respect to a central axis of the body.

4. The user input device of claim 3, wherein the two points of contact pressure are disposed no more than approximately 225° of each other with respect to the central axis.

5. The user input device of claim 1, wherein the one or more sensors each define a distinct trigger zone corresponding to a different possible point of contact pressure of the contact pressure arrangement.

6. The user input device of claim 5, wherein the controller determines that the contact pressure arrangement corresponds to the pinching action by:
    detecting a first grouping of one or more activated trigger zones; and
    detecting a second grouping of one or more activated trigger zones centered opposite the first grouping about the body.

7. The user input device of claim 6, wherein the controller determines that the contact pressure arrangement corresponds to the pinching action when:
    the first grouping includes only a single activated trigger zone and the second grouping includes two or more activated trigger zones; or
    the first grouping includes two or more activated trigger zones and the second grouping includes only a single activated trigger zone.

8. The user input device of claim 1, wherein the body is configured to be integrated into a medical imaging device.

9. The user input device of claim 1, wherein the controller is further operative to manipulate the control signal only while the contact pressure arrangement corresponds to the pinching action.

10. A method of controlling a device comprising:
    detecting, via one or more sensors on at least one surface, a contact pressure arrangement applied to a body of a user input device with at least first and second surfaces;
    determining via a controller in electronic communication with the one or more sensors that the contact pressure arrangement of three or more sensors corresponds to a pinching action; and
    recognizing the pinching action and enabling manipulating a control signal via the controller based at least in part on the contact pressure arrangement.

11. The method of claim 10, wherein determining via a controller in electronic communication with the one or more sensors that the contact pressure arrangement corresponds to a pinching action is independent of the orientation of the contact pressure arrangement being aligned with pre-determined fixed positions with respect to the body.

12. The method of claim 10, wherein determining via a controller in electronic communication with the one or more sensors that the contact pressure arrangement corresponds to a pinching action comprises:
   detecting via the controller that two points of contact pressure of the contact pressure arrangement are disposed at least approximately 135° of each other with respect to a central axis of the body.

13. The method of claim 12, wherein determining via a controller in electronic communication with the one or more sensors that the contact pressure arrangement corresponds to a pinching action further comprises:
   detecting via the controller that the two points of contact pressure are disposed no more than approximately 225° of each other with respect to a central axis of the body.

14. The method of claim 10, wherein the one or more sensors each define a distinct trigger zone corresponding to a different possible point of contact pressure of the contact pressure arrangement, and determining via a controller in electronic communication with the one or more sensors that the contact pressure arrangement corresponds to a pinching action further comprises:
   detecting via the controller a first grouping of one or more activated trigger zones; and
   detecting via the controller a second grouping of one or more activated trigger zones centered opposite the first grouping about the body.

15. The method of claim 14, wherein the controller determines that the contact pressure arrangement corresponds to the pinching action when:
   the first grouping includes only a single activated trigger zone and the second grouping includes two or more activated trigger zones; or
   the first grouping includes two or more activated trigger zones and the second grouping includes only a single activated trigger zone.

16. The method of claim 10, wherein the controller manipulates the control signal only while the contact pressure arrangement corresponds to the pinching action.

17. A non-transitory computer readable medium storing instructions that adapt a controller to:
   detect, via one or more sensors on at least one surface, a contact pressure arrangement of three or more sensors applied to a body with at least first and second surfaces of a user input device;
   determine that the contact pressure arrangement corresponds to a pinching action; and
   manipulate upon recognition of said pinching action enabling a control signal based at least in part on the contact pressure arrangement.

18. The non-transitory computer readable medium of claim 17, wherein the instructions further adapt the controller to determine that the contact pressure arrangement corresponds to the pinching action independently of the orientation of the contact pressure arrangement being aligned with pre-determined fixed positions with respect to the body.

19. The non-transitory computer readable medium of claim 17, wherein the instructions further adapt the controller to determine that the contact pressure arrangement corresponds to a pinching action by:
   detecting that two points of contact pressure of the contact pressure arrangement are disposed at least approximately 135° of each other with respect to a central axis of the body.

20. The non-transitory computer readable medium of claim 17, wherein the instructions further adapt the controller to manipulate the control signal only while the contact pressure arrangement corresponds to the pinching action.

* * * * *